(12) United States Patent
Benavent Bosch et al.

(10) Patent No.: US 8,318,141 B2
(45) Date of Patent: Nov. 27, 2012

(54) COSMETIC DEPILATORY COMPOSITION

(75) Inventors: Jose Benavent Bosch, Barcelona (ES); Marta Torres Fernandez, Barcelona (ES)

(73) Assignee: Church & Dwight Co., Inc., Princeton, NJ (US)

( * ) Notice: Subject to any disclaimer, the term of this patent is extended or adjusted under 35 U.S.C. 154(b) by 444 days.

(21) Appl. No.: 12/528,016

(22) PCT Filed: Feb. 21, 2008

(86) PCT No.: PCT/US2008/054565
§ 371 (c)(1),
(2), (4) Date: Sep. 14, 2009

(87) PCT Pub. No.: WO2008/103817
PCT Pub. Date: Aug. 28, 2008

(65) Prior Publication Data
US 2010/0021411 A1 Jan. 28, 2010

(30) Foreign Application Priority Data
Feb. 21, 2007 (ES) .................................. 200700448

(51) Int. Cl.
| | |
|---|---|
| A61K 8/18 | (2006.01) |
| A61Q 5/00 | (2006.01) |
| A61Q 7/00 | (2006.01) |
| A61Q 9/00 | (2006.01) |
| A61K 8/72 | (2006.01) |
| A61K 36/00 | (2006.01) |
| A61K 8/81 | (2006.01) |
| A61K 8/19 | (2006.01) |
| A01N 61/00 | (2006.01) |
| A01N 65/00 | (2009.01) |
| F16C 33/18 | (2006.01) |
| B29C 41/00 | (2006.01) |
| C08F 220/18 | (2006.01) |
| C08F 2/08 | (2006.01) |
| C08K 5/01 | (2006.01) |
| C08L 93/00 | (2006.01) |

(52) U.S. Cl. .................. 424/70.1; 424/70.11; 424/70.13; 424/70.16; 424/73; 424/74; 424/195.18; 424/725; 508/101; 524/798; 524/848; 524/878; 585/435; 585/600

(58) Field of Classification Search ................. 424/70.1, 424/70.11, 70.13, 70.16, 73, 74, 195.18, 424/725; 508/101; 524/798, 848, 878; 585/435, 585/600
See application file for complete search history.

(56) References Cited

U.S. PATENT DOCUMENTS

| | | | | |
|---|---|---|---|---|
| 6,369,126 | B1 * | 4/2002 | Cinelli et al. | 523/105 |
| 7,438,897 | B2 * | 10/2008 | Gupta | 424/70.1 |
| 2004/0175340 | A1 * | 9/2004 | Gupta | 424/70.1 |
| 2006/0134035 | A1 * | 6/2006 | Zheng et al. | 424/64 |
| 2007/0020205 | A1 * | 1/2007 | Blin et al. | 424/61 |
| 2007/0196309 | A1 * | 8/2007 | Tarletsky et al. | 424/70.12 |

FOREIGN PATENT DOCUMENTS

| | | |
|---|---|---|
| EP | 0795314 | 3/1997 |
| JP | 61212513 | 9/1986 |
| JP | 2001002539 | 1/2001 |
| WO | 2004014179 | 2/2004 |
| WO | 2005112876 | 12/2005 |

* cited by examiner

*Primary Examiner* — Richard Schnizer
*Assistant Examiner* — Jane C Oswecki
(74) *Attorney, Agent, or Firm* — Frenkel & Associates, P.C.; Allen R. Kipnes; Stephen B. Shear

(57) ABSTRACT

A cosmetic cold-wax depilatory composition is provided The depilatory composition comprises a hydrocarbon resin, from 50% to 99% by weight and a flexibilizer or plasticizer, from 0.5% to 10% by weight Methods of applying the composition to a strip of material for removal of hair without the need for heating are also provided.

15 Claims, No Drawings

COSMETIC DEPILATORY COMPOSITION

CROSS-REFERENCE TO RELATED APPLICATION

This application is related to Spanish Patent Application Serial No. 200700448 filed Feb. 21, 2007 and takes priority therefrom.

SUBJECT OF THE INVENTION

The present invention relates to a cosmetic depilatory composition, which comprises a hydrocarbon resin and a flexibilizer or plasticizer, that can be used for cold depilation.

BACKGROUND OF THE INVENTION

Presently, in both domestic and professional settings, wax depilation is one of the methods most often used for removing hair from different areas of the body to achieve the desired aesthetic and hygienic objectives.

For this purpose, hot, warm or cold waxes are used, which adhere firmly to the hair and permit it to be pulled out together with the hair follicle (commonly described as "by the root").

Hot waxes are solid at room temperature, are heated until they reach a sticky liquid state, and are applied using a spatula or special applicator. The applied hot waxes are allowed to cool and are peeled off.

Warm waxes are semisolid at room temperature, are slightly heated until they reach a sticky liquid state, and are applied using a spatula or special applicator. The warm waxes must be removed with the aid of strips of nonwoven cloth, cellophane or other materials.

Cold waxes are semi-solid at room temperature, are sold preapplied to strips of non-woven cloth, cellophane or other materials. These strips with preapplied wax are applied directly without need of heating and are peeled off. At the present time, the composition of these cold waxes is based on colophony (pine resin), colophony derivatives, paraffin, silica, oils, microcrystalline waxes, beeswax or polymers, among other ingredients, which fulfill different functions in the formulation of cold wax. The main components (those responsible for the adhesion) are colophony and its derivatives. Colophony is a solid, dark brown or yellowish resin, obtained as a residue from the distillation of turpentine. Due to the intrinsic nature of pine resin and its derivatives, cold waxes acquire a characteristic odor (typical of colophony and reminiscent of turpentine) and color (dark golden-brown) that make it difficult or impossible to color and perfume as demanded by cosmetic market trends. There also exist on the market some cold waxes based on glucose and other saccharides derived from sugar, which in the manufacturing process acquire a characteristic odor (burnt sugar) and color (dark golden-brown) that also make it difficult or impossible to color and perfume as demanded by cosmetic market trends.

The present invention describes a cosmetic depilatory composition of odorless, colorless, transparent cold wax, which can be easily colored and perfumed, permitting the development of more aesthetic and sophisticated products, in line with the cosmetic trends of the current market.

DESCRIPTION OF THE INVENTION

The subject of the present invention is a cosmetic cold-wax depilatory composition which comprises the following ingredients:
(a) hydrocarbon resin, from 50% to 99% by weight;
(b) flexibilizer or plasticizer, from 0.5% to 10% by weight, where said composition is preapplied to strips.

In one embodiment of the invention, the hydrocarbon resin is chosen from the group consisting in hydrogenated styrene-methylstyrene-indene copolymers, olefin-styrene copolymers, and hydrogenated polycyclopentadiene.

In one embodiment of the invention, the hydrogenated styrene-methylstyrene-indene copolymer is chosen between Regalite™ 1090 or Regalite™ 1010 from the Eastman Chemical Company.

In one embodiment of the invention, the olefin-styrene copolymer is Escorez™ 2520 from Exxon Mobil Chemical.

In one embodiment of the invention, the hydrogenated polycyclopentadiene is Escorez™ 5380 from Exxon Mobil Chemical.

In one embodiment of the invention, the flexibilizer or plasticizer is chosen from the group consisting of alkyl methicones, olefins, microcrystalline waxes, synthetic beeswaxes, and dimeric alkyl esters of synthetic long-chain fatty alcohols.

In one embodiment of the invention, the alkyl methicone is Dow Corning's C30-45 alkyl methicone.

In one embodiment of the invention, the olefin is Dow Corning's C30-45, olefin.

The mixture of C30-45 dimethicone and C30-45 olefin is Dow Corning's AMS-C30 wax.

In one embodiment of the invention, the microcrystalline wax is chosen from among microcrystalline waxes that have a melting point between 70° C. and 90° C.

In one embodiment of the invention, the synthetic beeswax is Koster Keunen's KesterWax K80H.

In one embodiment of the invention, the dimeric alkyl ester of synthetic long-chain fatty alcohols is Koster Keunen's KesterWax K82D.

The cosmetic depilatory composition of the present invention is a semisolid wax suitable for preapplication to strips, which permits the production of odorless, colorless, transparent cold wax strips that can easily be perfumed and colored, resulting in waxes that are more esthetic and sophisticated, and more oriented toward the cosmetic trends of the current market, unlike the current products which have the characteristic odor and color of colophony and/or its derivatives, and are difficult to color and perfume.

In one embodiment of the invention, the cosmetic depilatory composition additionally comprises:
(c) pigments and colorants of various kinds, from 0.0001% to 3% by weight
(d) perfume, from 0.0001% to 3% by weight
(e) active cosmetic ingredients, natural or synthetic, of different kinds and different cosmetic properties, such as vegetable oils, essential oils, or plant-derived extracts, from 0.0001% to 3% by weight.

In one embodiment of the invention, the pigments and colorants are chosen from the group consisting of chlorophyll, carmine, reflective pigments with a base of calcium aluminum borosilicate and/or lacquers predispersed in castor oil.

In one embodiment of the invention, the active cosmetic ingredients, natural or synthetic, are chosen from a group composed of liposoluble extracts (oils and waxes) of fruits, flowers, plants, and/or essential oils.

EXAMPLES

Some non-limiting examples of the invention are described below:

Example 1

Cold Wax with Reflective Particles 1

A depilatory composition comprising the following ingredients was prepared:

| Ingredients | % by weight |
| --- | --- |
| Hydrogenated styrene-methylstyrene-indene copolymer | 85-99 |
| C30-45 alkyl methicone | 0.5-10 |
| C30-45 olefin | 0.5-10 |
| Reflective pigments with a base of calcium aluminum borosilicate | 0.0001-3 |
| Pigments, colorants | 0.0001-3 |
| Perfume | 0.0001-3 |
| Active cosmetic ingredients, natural or synthetic | 0.0001-3 |

The procedure for obtaining said composition was as follows. All components of the mixture (excepting the pigments, colorants, perfume and active ingredients) were heated to a temperature between 100° C. and 120° C., with continual stirring in order to assure a homogeneous mixture and to avoid the incorporation of air. Once a transparent, colorless, homogeneous liquid mixture was obtained, the rest of the components (pigments, colorants, perfume and active ingredients) were added and cooling was initiated, without discontinuing the stirring to avoid the incorporation of air.

Example 2

Odorless, Colorless, Transparent Cold Wax 1

A depilatory composition comprising the following ingredients was prepared according to the procedure described in Example 1:

| Ingredients | % by weight |
| --- | --- |
| Hydrogenated styrene-methylstyrene-indene copolymer | 85-99 |
| C30-45 alkyl methicone | 0.5-10 |
| C30-45 olefin | 0.5-10 |

Example 3

Odorless, Colorless, Transparent Cold Wax 2

A depilatory composition comprising the following ingredients was prepared according to the procedure described in Example 1:

| Ingredients | % by weight |
| --- | --- |
| C5-6 olefin-styrene copolymer | 50-65 |
| Hydrogenated polycyclopentadiene | 40-55 |
| Microcrystalline wax | 0.5-10 |

Example 4

Odorless, Colorless, Transparent Cold Wax 3

A depilatory composition comprising the following ingredients was prepared according to the procedure described in Example 1:

| Ingredients | % by weight |
| --- | --- |
| Hydrogenated styrene-methylstyrene-indene copolymer | 85-99 |
| Microcrystalline wax | 0.5-10 |

Example 5

Odorless, Colorless, Transparent Cold Wax 4

A depilatory composition comprising the following ingredients was prepared according to the procedure described in Example 1:

| Ingredients | % by weight |
| --- | --- |
| Hydrogenated styrene-methylstyrene-indene copolymer | 85-99 |
| Synthetic beeswax | 0.5-10 |

Example 6

Odorless, Colorless, Transparent Cold Wax 5

A depilatory composition comprising the following ingredients was prepared according to the procedure described in Example 1:

| Ingredients | % by weight |
| --- | --- |
| Hydrogenated styrene-methylstyrene-indene copolymer | 85-99 |
| Dimer linoleate of C20-40 | 0.5-10 |

What is claimed is:

1. A cosmetic cold-wax depilatory composition, comprising: (a) hydrocarbon resin selected from the group consisting of hydrogenated styrene-methylstyrene-indene copolymers, C5-6 olefin-styrene copolymers, hydrogenated polycyclopentadiene, and combinations thereof, from 85% to 99% by weight of the total composition, and (b) flexibilizer or plasticizer, from 0.5% to 10% by weight of the total composition.

2. The cosmetic cold-wax depilatory composition according to claim 1, characterized in that the flexibilizer or plasticizer is chosen from a group consisting of alkyl methicones, olefins, microcrystalline waxes, synthetic beeswaxes, dimeric alkyl esters of synthetic long-chain fatty alcohols, and combinations thereof.

3. The cosmetic cold-wax depilatory composition according to claim 2, characterized in that the flexibilizer or plasticizer is an alkyl methicone or olefin or mixture thereof.

4. The cosmetic cold-wax depilatory composition according to claim 2, characterized in that the flexibilizer or plasticizer is a microcrystalline wax having a melting point between 70° C. and 90° C.

5. The cosmetic cold-wax depilatory composition according to claim 2, characterized in that the flexibilizer or plasticizer is a synthetic beeswax.

6. The cosmetic cold-wax depilatory composition according to claim 2, characterized in that the flexibilizer or plasticizer is a dimeric alkyl ester of synthetic long-chain fatty alcohols.

7. The cosmetic cold-wax depilatory composition according to claim 1, characterized in that it additionally comprises:
(c) pigments and colorants, from 0.0001% to 3% by weight of the total composition;
(d) perfume, from 0.0001% to 3% by weight of the total composition;
(e) active cosmetic ingredients, natural or synthetic, selected from vegetable oils, essential oils, or plant-derived extracts, from 0.0001% to 3% by weight of the total composition.

8. The cosmetic cold-wax depilatory composition according to claim 7, characterized in that the pigments and colorants are chosen from the group consisting of chlorophyll, carmine, reflective pigments with a base of calcium aluminum borosilicate and lacquers predispersed in castor oil.

9. The cosmetic cold-wax depilatory composition according to claim 7, characterized in that the active cosmetic ingredients, natural or synthetic, are chosen from the group consisting of liposoluble extracts of fruits, flowers, plants, and essential oils.

10. A method of removing hair from a body by cold depilation comprising applying onto a portion of the body that contains hair a strip of material having preapplied thereon a cold-wax depilatory composition comprising (a) hydrocarbon resin selected from the group consisting of hydrogenated styrene-methylstyrene-indene copolymers, $C_{5-6}$ olefin-styrene copolymers, hydrogenated polycyclopentadiene, and combinations thereof, from 85% to 99% by weight of the total composition, and (b) flexibilizer or plasticizer, from 0.5% to 10% by weight of the total composition, and peeling off said strip of material from skin.

11. The method of claim 10, wherein said strip of material is applied to said skin without heating.

12. The method of claim 10, wherein said strip of material is a nonwoven cloth or cellophane.

13. The method of claim 10, wherein said flexibilizer or plasticizer is chosen from the group consisting of alkyl methicones, olefins, microcrystalline waxes, synthetic beeswaxes, and dimeric alkyl esters of synthetic long-chain fatty alcohols.

14. The method of claim 10, wherein said cold-wax depilatory composition additionally comprises:
(c) pigments and colorants from 0.0001% to 3% by weight of the total composition;
(d) perfume, from 0.0001% to 3% by weight of the total composition;
(e) active cosmetic ingredients, natural or synthetic, selected from vegetable oils, essential oils, or plant-derived extracts, from 0.0001% to 3% by weight of the total composition.

15. A strip of material having applied thereto a cold-wax depilatory composition comprising:
(a) hydrocarbon resin selected from the group consisting of hydrogenated styrene-methylstyrene-indene copolymers, C5-6 olefin-styrene copolymers, hydrogenated polycyclopentadiene, and combinations thereof, from 85% to 99% by weight of the total composition, and
(b) flexibilizer or plasticizer, from 0.5% to 10% by weight of the total composition.

* * * * *